(12) United States Patent
Kang et al.

(10) Patent No.: US 7,405,267 B2
(45) Date of Patent: Jul. 29, 2008

(54) METHOD FOR PURIFYING TEICOPLANIN $A_2$

(75) Inventors: Tae-Won Kang, Seoul (KR);
Byoung-Taek Choi, Seoul (KR);
Gang-Sun Choi, Kyunggi-do (KR);
Yong-Rack Choi, Kyunggi-do (KR);
Sung-Ho Hwang, Incheon (KR)

(73) Assignee: CKD BIO Corp., Seoul (KR)

( * ) Notice: Subject to any disclaimer, the term of this patent is extended or adjusted under 35 U.S.C. 154(b) by 710 days.

(21) Appl. No.: 10/621,353

(22) Filed: Jul. 18, 2003

(65) Prior Publication Data

US 2004/0024177 A1  Feb. 5, 2004

(30) Foreign Application Priority Data

Jul. 19, 2002  (KR) .................. 10-2002-0042425

(51) Int. Cl.
*C07K 1/14* (2006.01)
*C07K 1/18* (2006.01)
*C07K 1/20* (2006.01)
*C07K 1/22* (2006.01)
*C12P 19/28* (2006.01)
*C07K 5/12* (2006.01)
*C07K 5/02* (2006.01)

(52) U.S. Cl. .................. 530/344; 530/317; 530/332; 435/85

(58) Field of Classification Search .................. 435/85, 435/183; 530/344, 317, 332
See application file for complete search history.

(56) References Cited

U.S. PATENT DOCUMENTS

| 4,239,751 A | 12/1980 | Coronelli et al. |
| 4,542,018 A | 9/1985 | Borghi et al. |
| 4,594,187 A * | 6/1986 | Strazzolini et al. .......... 530/332 |
| 4,845,194 A | 7/1989 | Glass et al. |
| 5,539,087 A * | 7/1996 | Restelli et al. .............. 530/412 |
| 6,391,851 B1 * | 5/2002 | Sawai et al. ................. 514/8 |

FOREIGN PATENT DOCUMENTS

| EP | 479086 | 9/1995 |
| KR | 200066479 | 11/2000 |

OTHER PUBLICATIONS

Parenti et al., "Teichomycins, New Antibiotics from *Actinoplanes teichomyceticus* Nov. Sp.", The Journal of Antibiotics, Apr. 1978, pp. 276-283.

* cited by examiner

*Primary Examiner*—Sandra E. Saucier
*Assistant Examiner*—Susan Hanley
(74) *Attorney, Agent, or Firm*—Greenblum & Bernstein, P.L.C.

(57) ABSTRACT

Disclosed is a method for purifying teicoplanin $A_2$ comprising: (i) a primary pre-purification step of purifying a filtrate of fermentation broth of a strain using a synthetic adsorbent; (ii) a secondary pre-purification step of purifying the primary pre-purification solution using a cation exchange resin having a high cross-linkage, a catalytic resin or a chelate resin; (iii) a final purification step of purifying the secondary pre-purification solution using a reversed phase resin; and (iv) a powder-forming step. According to the present invention, it is possible to obtain teicoplanin $A_2$ with a higher purity through a relatively simple process without using an excessive amount of an organic solvent.

8 Claims, No Drawings

METHOD FOR PURIFYING TEICOPLANIN $A_2$

BACKGROUND OF THE INVENTION

1. Field of the Invention

The present invention relates to a method for purifying teicoplanin $A_2$ which is a glycopeptide antibiotics.

2. Background of the Related Art

The glycopeptide antibiotics show excellent activity against superbacteria which recently comes to the fore as a serious problem to public health and are known to inhibit multiplication of bacteria by disrupting cell wall synthesis of pathogenic gram positive bacteria. Teicoplanin $A_2$, is particularly in a great demand since it is excellent in the medicinal effect but has a low toxicity and a long half life.

Production of teicoplanin $A_2$ mainly depends on purification by fermentation since it is hardly synthesized in a chemical method. One of representative strains which have been used in production of teicoplanin includes *Actinoplanes teichomyceticus* ATCC 31121 (J. Antibiotics, 276-283, 1978). This strain produces A8327 factor B and A8327 factor C, as well as teicoplanin $A_1$, teicoplanin $A_2$ and teicoplanin $A_3$ through a fermentation process. Therefore, methods which can selectively purify teicoplanin $A_2$ from the fermentation broth of the strain have been continuously developed.

According to the procedure described in U.S. Pat. No. 4,239,751, teicoplanin is isolated from the fermentation broths by filtering it, mixing with a water-insoluble organic solvent at pH 3.5 to dissolve an antibiotic mixture, extracting twice, and condensing the extract at a lower temperature until precipitates of the antibiotic mixture are formed, followed by filtering to recover the precipitates. Then, in order to recover the antibiotic substances remaining in the mycelia, an additional extract using an aqueous solution of acetone is conducted. The precipitate thus obtained contains A8327 factors as well as three types of teicoplanin. Accordingly, the precipitates are subjected to a solvent system to remove A8327 factors and to a chromatography on Sephadex LH 20 to specifically isolate teicoplanin $A_2$.

The above method has defects, related to environmental pollution and an economical burden, in that the final product contains diverse organic solvents accumulated therein due to the use of the organic solvent through several steps and an expensive separation resin such as Sephadex LH 20 should be used to obtain teicoplanin $A_2$, though it enables us to obtain teicoplanin with a high purity.

U.S. Pat. No. 4,542,018 discloses a method for producing pure single factors of teicoplanin $A_2$, teicoplanin $A_{2-1}$, $A_{2-2}$, $A_{2-3}$, $A_{2-4}$ and $A_{2-5}$ by reversed phase resin chromatography of teicoplanin $A_2$ obtained by the method according to U.S. Pat. No. 4,239,751.

However, since the method of this patent also uses the expensive reversed phase resin having a small particle size, it cannot be used for the industrial purposes of mass production and still has the problems involved in the method of U.S. Pat. No. 4,239,751.

Meanwhile, U.S. Pat. No. 4,239,751 discloses a method for producing teicoplanin $A_2$, in which a fermentation broth is mixed with a water-miscible solvents such as acetonitrile, acetone, propanol, methylethylketone, etc. without filtration to isolate teicoplanin $A_2$ from the fermentation broth and the resulting solution is condensed, left at a low temperature until precipitates are formed, followed by filtration to recover the precipitates. This method is simpler than that of U.S. Pat. No. 4,239,751, since one step is omitted.

However, the method has disadvantages in that it uses an excessive amount of organic solvents, instead of a filtration process, to separate the filtrate from the mycelia, causing of solvent accumulation and much cost is taken to recover and separate the used solvent mixture.

According to the method disclosed in EP Pat. No. 0479086, in order to increase extraction efficiency of teicoplanin $A_2$, the fermentation broth is adjusted to a predetermined pH, prior to two filtration processes. The filtrate of the fermentation broth is loaded on a polyamide resin and the eluate is extracted with an excessive amount of acetone and left to stand for 3 hours. The supernatant is decanted and the rest is filtered. The resulting cake is washed with acetone to recover teicoplanin $A_2$.

By the method, it is possible to obtain teicoplanin $A_2$ with HPLC purity of 85% at yield of 74.3%. However, such purity is low to be used in production of medicine. Also, it still has the problem of solvent accumulation, since it uses an excessive amount of acetone in diverse steps.

U.S. Pat. No. 4,845,194 discloses a method for producing teicoplanin, in which a cation exchange resin having a cross-linkage of 2% or less is added to the fermentation broth to adsorb teicoplanin to the resin and a 100 mesh sieve is used to separate the mycelia from the resin. Then, the resin is washed with purified water, followed by elution to recover teicoplanin.

However, the cation exchange resin having a cross-linkage of 2% or less which is used for filtration has chemical defects that it can be degraded in oxidation resistance, volume change, exchange capability and physical defects that it can easily break, causing reduction in its life span. Thus, this method has a disadvantage in that the resin should be frequently exchanged, thereby causing an increase in the cost.

Korean Patent Publication No. 2000-0066479 discloses a method for producing teicoplanin $A_2$, in which a fermentation broth is adjusted to pH 11 and centrifuged, and the supernatant is adsorbed onto a synthetic adsorbent resin such as XAD-16, HP-20 and activated carbon or silica gel, eluted with a 50 to 80% methanol solution and purified under reduced pressure to obtain teicoplanin $A_2$ as crude powder. The crude teicoplanin $A_2$ is dissolved in a solution of sodium acetate and purified by sugar affinity chromatography.

According to this method, there may occur problems related to stability of teicoplanin in the vacuum distillation step to remove the methanol solution, after elution from the synthetic adsorbent resin. Also, since it uses an expensive resin and organic solvent, it is not preferably applicable in mass-production.

Therefore, there still remain demands for inventions directed to a method that can be used to mass produce high purity teicoplanin $A_2$ without using an excessive amount of organic solvents or an expensive resin.

SUMMARY OF THE INVENTION

Therefore, it is an object of the present invention to provide a method for purifying teicoplanin $A_2$ with a high purity by a simple process without using an excessive amount of organic solvents.

In accordance with the present invention, the above and other objects can be accomplished by the provision of the method for purifying teicoplanin $A_2$ according to the present invention comprises:

(i) a primary pre-purification step of purifying a filtrate of fermentation broth using a synthetic adsorbent;

(ii) a secondary pre-purification step of purifying the primary pre-purification solution using a cation exchange resin having a high cross-linkage, a catalytic resin or a chelate resin;

(iii) a final purification step of purifying the secondary pre-purification solution using a reversed phase resin; and (iv) a powder-forming step.

DETAILED DESCRIPTION OF THE PREFERRED EMBODIMENT

The present invention is directed to a method for purifying teicoplanin $A_2$.

Now, the method for purifying teicoplanin $A_2$ according to the present invention will be described in detail hereinafter for respective steps.

Firstly, a strain which can produce teicoplanin $A_2$ is cultured for fermentation. In the method for purifying teicoplanin $A_2$ according to the present invention, the strain *Actinoplanes teichomyceticus* ATCC 31121 is preferably used as the teicoplanin $A_2$ producing strain.

In the primary pre-purification step, the filtrate of fermentation broth is adjusted to pH prior to introducing a synthetic adsorbent. According to the method for purifying teicoplanin $A_2$ of the present invention, in order to increase the purification efficiency of teicoplanin $A_2$ for the synthetic adsorbent, the filtrate is adjusted to pH in the range of 4 to 9, preferably in the range of 5 to 7.

The synthetic adsorbent is a high molecular polymer which has a high porosity and a large micropore specific surface area and thus, can adsorb a large molecular weight and removes a coloring substance in a filtrate.

Examples of the synthetic adsorbent which can be used in the method according to the present invention include high porous styrene type synthetic adsorbents, high porous styrene type synthetic adsorbents having bromine chemically substituted, high porous styrene/divinyl polymers, macroreticularly cross-linked polymer, macroreticularly cross-linked aliphatic polymer, macroreticularly cross-linked aromatic polymer, methacrylic synthetic adsorbents and carbonaceous synthetic adsorbents comprising a high porous styrene/divinyl benzene ion exchange resin.

Concretely, examples of commercially available synthetic adsorbents include high porous styrene type synthetic adsorbents having bromine chemically substituted (sold under the trademark DIAION SP207), high porous styrene type synthetic adsorbents (sold under the trademarks (DIAION SP700, DIAION SP825, DIAION SP850), methacrylic synthetic adsorbents (sold under the trademark DIAION HP2MG (Mitsubishi Chemical co.)), AMBERLITE XAD 4 and AMBERLITE XAD 1600T, AMBERLITE XAD 7, AMBERSORB 563, AMBERSORB 572, AMBERSOPB 600 (ROHM and HAAS co.), LEWATIT VP OC 1064, LEWATIT VP OC 1066 and LEWATIT EP 63 (Bayer co.)).

A filtrate of fermentation broth is purified by passing it through a column packed with one selected from the above-listed and the column is washed with purified water. Then, an eluent at a proper pH is eluted through column to separate teicoplanin from the resin.

The pH of the eluent determines the purification efficiency of teicoplanin. According to the present invention, in the primary pre-purification step, purified water in the range of 10 to 13, preferably purified water in the range of pH 10.5 to 12 is used as an eluent. Also, purified water containing acetone may be used. Preferably, acetone is contained in a concentration of 50 to 80%. In the above-described pH range, only teicoplanin is specifically isolated into the eluent, while other organic substances remains adsorbed onto the synthetic adsorbent, whereby the subsequent procedures can be readily performed.

Then, in the secondary pre-purification step, the primary pre-purification solution is subjected to a chromatography using a cation exchange resin, catalytic resin or chelate resin having a high cross-linkage. The cation exchange resin, catalytic resin and chelate resin which can be used according to the present invention have a cross-linkage of over 8%. Also, preferably, the resins comprises a high porous polystyrene/divinyl polymer and is of a gel or porous type having a sulphonate or iminoacetate group as an exchange group.

Concretely, the resins includes, among the commercially available, gel-type cation exchange resins (sold under the trademarks DIAION SK1B, DIAION UBK555 (Mitsubishi Chemical co.), AMBERLITE CR1310 NA, AMBERJET 200H (Rohn & Haas co.), LEWATIT VP OC 1800, LEWATIT MDS1368 NA (Bayer co.), PUROLITE PCR833CA (Purolite co.), MFG 210 and MFG 250 (Finex co.)), porous-type cation exchange resins (sold under the trademarks DIAION PK216 (Mitsubishi Chemical co.), AMBERLITE 200C NA, AMBERLITE CG50 (Rohn & Haas co.), LEWATIT VP OC 1812 (Bayer co.), and PUROLITE C145 (Purolite co.)), AMBERLYST 131 WET (gel-type strongly acid polymer resin), AMBERLYST 232 WET (gel-type strongly acid polymer resin) (Rohn & Haas co.) and LEWATIT K1221 (Bayer co.)), porous-type catalytic resins (sold under the trademarks TRILITE SPC 160H (a strongly acidic porous resin comprising a styrene polymer matrix), and TRILITE SPC 180H (a strongly acidic cation exchange resins comprising a porous styrene polymer matrix) (Samyang co.)), and porous-type chelate resins (sold under the trademarks DIAION CR11 and DIAION CR20 (Mitsubishi Chemical co.)).

One selected from the above-described resins is packed in a column and a filtrate of fermentation broth is passed through the column. Here, one of the most important factors to adsorb teicoplanin to the resin is pH upon regeneration of the resin. According to the present invention, the resin is regenerated by sequentially washing it with sodium hydroxide and a weak acid such as acetic acid or diluted hydrochloric acid and then, purified water so that the final eluate of purified water is in the range of 4.5 to 7.0.

After completion of loading a filtrate of fermentation broth on the column, the column is washed with purified water and teicoplanin adsorbed onto the column is eluted out with an eluent having a proper pH. Here, the elution of teicoplanin is determined by the pH of the eluent. According to the present invention, the eluent used in the secondary pre-purification is purified water in the range of pH 10 to 13, preferably purified water in the range of pH 10.5 to 12.

According to the method for purifying teicoplanin $A_2$ of the present invention, when the pre-purification steps are completed, impurities such as those that affect adversely on the subsequent reversed phase resin chromatography, for example, organic solvents, as well as most of coloring substances which have initially contained in the filtrate of broth, are removed, whereby it is possible to obtain a pre-purification solution of teicoplanin with a HPLC purity of over 40%.

Therefore, according to the method for purifying teicoplanin $A_2$ of the present invention, since a pre-purification solution of teicoplanin has a purity of over a predetermined level, it is possible to readily adsorb teicoplanin to a resin in the final purification without hindrance of other impurities.

The pre-purification solution of teicoplanin obtained from the pre-purification steps is then subjected to the final purification using reverse phase resin without separate adjustment of pH.

The reversed phase resin which can be used in the method according to the present invention comprises silica containing non-polar side chain having 1 to 18 carbon and having a particle size of 15 to 150 μm. Examples of the reversed phase resin which can be preferably used in the present invention include SK-GEL ODS S-15/30 (Soken co.)), FLASH KP-C18-HS (Biotage co.)), DAISOGEL 3001A (Daiso co.)) and DMS DM 1020 (Shiseido co.)).

One selected from the above-described resins is packed in a column and the pre-purification solution is passed through the column. The column is washed with purified water and teicoplanin adsorbed onto the resin is eluted with an aqueous solvent mixture as an eluent. In the method for purifying teicoplanin $A_2$ according to the present invention, purified water containing an organic solvent, preferably purified water containing in a concentration of 20 to 30%, is used as the eluent. Particularly, purified water containing acetone or acetonitrile in a concentration of 23 to 27% is used.

According to the method for purifying teicoplanin $A_2$ of the present invention, when the final purification is completed, it is possible to obtain a purification solution of teicoplanin having a high purity of over 95%. Only 3% or less of teicoplanin $A_3$, which is a critical analogue of teicoplanin $A_2$, is contained in the final purification solution, which indicates the high purity of the purification solution.

Subsequently, in the powder-forming step, the final purification solution is adsorbed onto the synthetic adsorbent used in the pre-purification steps or the reversed phase resin used in the final purification. The method and conditions for adsorption are the same as those for the pre-purification steps and the final purification.

As an eluent, purified water containing acetone or acetonitrile in a concentration of 50 to 80% is used to elute teicoplanin adsorbed on to the resin. The resulting eluate was concentrated in vacuum to remove the organic solvents and lyophilized to obtain high purity teicoplanin $A_2$ as powder.

Therefore, by the method for purifying teicoplanin $A_2$ according to the present invention, since extraction processes using an organic solvent is substituted with purification steps by a synthetic adsorbent and a resin, it is possible to prevent low efficiency phenomena such as quality degradation of teicoplanin $A_2$ due to residual organic solvents, environmental pollution and economical waste such as increase in disposal cost.

Also, by the method for purifying teicoplanin $A_2$ according to present invention, it is possible to obtain teicoplanin $A_2$ with a much higher purity through a relatively simple process without using an excessive amount of an organic solvent.

Thus, the method for purifying teicoplanin $A_2$ according to the present invention can be usefully used to industrially mass produce teicoplanin $A_2$.

Now, the present invention will be described in detail by the following examples, but it should be understood that it is not limited thereto.

EXAMPLE 1

Pre-purification of Teicoplanin $A_2$ Using a Synthetic Adsorbent (Sold Under the Trademark AMBERLITE XAD 1600T) and a Chelate Resin (Sold Under the Trademark AMBERLYST 232 WET)

Teicopianin $A_2$ was pre-purified using the synthetic adsorbent (sold under the trademark AMBERLITE XAD 1600T) and the chelate resin (sold under the trademark AMBERLYST 232 WET)

As a sample to purify teicoplanin, 1 l of culture filtrate (pH 7) containing about 0.9 g of teicoplanin $A_2$ was prepared.

For the primary pre-purification step, 150 ml of the synthetic adsorbent (sold under the trademark AMBERLITE XAD 1600T (ROHM and HAAS co.)) was packed in a chromatography column having a diameter of 4 cm and a length of 12 cm and the culture filtrate was loaded on the column at a flow rate of 2.5 ml/min.

The column was washed with purified water at room temperature and purified water which had been adjusted to pH 12 using sodium hydroxide (NaOH) was eluted through the column. The column used in the above procedure was regenerated with 200 ml of 1M NaOH solution and then, washed with 400 ml of purified water.

The primary purification solution obtained from the above-described procedures was subjected to HPLC to measure its purity. As a result, it was found to contain 0.8 g of teicoplanin $A_2$ with 27% purity.

For the secondary pre-purification, 50 ml of a sample containing about 0.5 g of teicoplanin $A_2$ was prepared.

100 ml of the chelate resin (sold under the trademark AMBERLYST 232 WET (ROHM and HAAS co.)) was packed in a chromatography column having a diameter of 4 cm and a length of 12 cm. The column was washed with sodium hydroxide and then acetic acid solution to equilibrate the resin. Purified water was eluted through the column and the eluent was checked to pH 6.45.

The sample solution was loaded on the column at a flow rate of 1.6 ml/min. The column was washed with purified water at room temperature and purified water which had been adjusted to pH 12 using sodium hydroxide (NaOH) was eluted through the column. The column used in the above procedure was regenerated with 150 ml of 1M NaOH solution and washed with 400 ml of purified water, 150 ml of 1M acetic acid and solution then, 200 ml of purified water.

The secondary purification solution obtained from the above-described procedures was subjected to HPLC to measure its purity. As a result, it was found to contain 0.46 g of teicoplanin $A_2$ with 43% purity.

Therefore, it was noted that by using the method for purifying teicoplanin $A_2$ according to the present invention, it is possible to obtain a pre-purification solution containing teicoplanin $A_2$ with a purity of over a predetermined level from a culture filtrate, even in a pre-purification step.

EXAMPLE 2

Pre-purification of Teicoplanin $A_2$ Using Synthetic Adsorbent (Sold Under the Trademark LEWATIT VP OC 1064) and Catalytic Resin (Sold Under the Trademark TRILITE SPC 400LH)

Teicoplanin $A_2$ was pre-purified using the synthetic adsorbent (sold under the trademark LEWATIT VP OC 1064) and the catalytic resin (sold under the trademark TRILITE SPC 400LH).

As a sample to purify teicoplanin, 1 2 of culture filtrate (pH 7) containing about 0.8 g of teicoplanin $A_2$ was prepared.

For the primary pre-purification step, 150 ml of the synthetic adsorbent (sold under the trademark LEWATIT VP OC 1064 (Bayer co.)) was packed in a chromatography column having a diameter of 4 cm and a length of 12 cm and the culture filtrate was loaded on the column at a flow rate of 2.5 ml/min.

The column was washed with 150 ml of purified water containing 10% acetone and purified water containing 50% acetone was eluted through the column. The column used in the above procedure was regenerated with 200 ml of 1M NaOH solution and then, washed with 400 ml of purified water.

The primary purification solution obtained from the above-described procedures was subjected to HPLC to measure its purity. As a result, it was found to contain 0.75 g of teicoplanin $A_2$ with 29% purity.

Subsequently, for the secondary pre-purification, 50 ml of a sample containing about 0.6 g of teicoplanin $A_2$ was prepared.

100 ml of the catalytic resin (sold under the trademark TRILITE SPC 400LH (Samyang co.)) was packed in a chromatography column having a diameter of 4 cm and a length of 12 cm. The column was washed with sodium hydroxide and then, diluted hydrochloric acid solution to equilibrate the resin. Purified water was eluted through the column and the eluent was checked to pH 5.87.

The sample solution was loaded on the column at a flow rate of 1.6 ml/min. The column was washed with purified water at room temperature and purified water which had been adjusted to pH 12 using sodium hydroxide (NaOH) solution was eluted through the column. The column used in the above procedure was regenerated with 150 ml of 1M NaOH solution and washed with 100 ml of purified water, 150 ml of 0.5M hydrochloric acid and then, 200 ml of purified water.

The secondary purification solution obtained from the above-described procedures was subjected to HPLC to measure its purity. As a result, it was found to contain 0.56 g of teicoplanin $A_2$ with 48% purity.

Therefore, as shown in Example 1 and Example 2, it was noted that by using the method for purifying teicoplanin $A_2$ according to the present invention, it is possible to obtain a pre-purification solution containing teicoplanin $A_2$ with a purity of over a predetermined level from a culture filtrate, even after a pre-purification step.

EXAMPLE 3

Preparation of High Purity Teicoplanin $A_2$ Purification Solution Using a Synthetic Adsorbent (Sold Under the Trademark DIAION HP2MG), a Chelate Resin (Sold Under the Trademarks DIAION CR11) and a Reversed Phase Resin (Sold Under the Trademark KP-C18-HS Reversed Phase Resin FLASH 75M Cartridge)

A high purity teicoplanin $A_2$ purification solution was prepared using the method for purifying teicoplanin $A_2$ according to the present invention.

As a sample to purify teicoplanin, 21 l of culture filtrate (pH 7) containing 25.3 g of teicoplanin was prepared.

For the primary pre-purification step, 8 l of the synthetic adsorbent (sold under the trademark DIAION HP2MG (Mitsubishi Chemical co)) was packed in a chromatography column having a diameter of 16 cm and a length of 40 cm and the culture filtrate was loaded on the column at a flow rate of 133 ml/min.

The column was washed with 8 l of purified water containing 10% acetone and purified water containing 50% acetone was eluted through the column. The column used in the above procedure was regenerated with 12 l of 1M NaOH solution and then, washed with 16 l of purified water.

The primary purification solution obtained from the above-described procedures was subjected to HPLC to measure its purity. As a result, it was found to contain 24 g of teicoplanin $A_2$ with 28% purity.

For the secondary pre-purification, 370 ml of a sample solution containing about 2.3 g of teicoplanin $A_2$ was prepared.

100 ml of the chelate resin (sold under the trademark DIAION CR11 (Mitsubishi Chemical co.)) was packed in a chromatography column having a diameter of 4 cm and a length of 12 cm. The column was washed with sodium hydroxide and then acetic acid solution to equilibrate the resin. Purified water was eluted through the column and the eluent was checked to pH 6.49.

The sample solution was loaded on the column at a flow rate of 1.6 ml/min. The column was washed with purified water at room temperature and purified water which had been adjusted to pH 12 using sodium hydroxide (NaOH) solution was eluted through the column. The column used in the above procedure was regenerated with 150 ml of 1M NaOH solution and washed with 100 ml of purified water, 150 ml of 1M acetic acid and then, 200 ml of purified water.

The secondary purification solution obtained from the above-described procedures was subjected to HPLC to measure its purity. As a result, it was found to contain 2.18 g of teicoplanin $A_2$ with 52.6% purity.

Subsequently, for the final purification, 10 ml of a sample solution containing about 0.7 g of teicoplanin $A_2$ was prepared.

The sample solution was loaded on the reversed phase resin (sold under the trademark KP-C18-HS reversed phase resin FLASH 75M cartridge (Biotage co.)) at a flow rate of 100 ml/min. The column was washed with purified water at room temperature and purified water containing 27% acetonitrile was eluted through the column. The column used in the above procedure was regenerated with 900 ml of 90% methanol and washed with 1000 ml of purified water.

The purification solution obtained from the above-described procedures was subjected to HPLC to measure its purity. As a result, it was found to contain 0.59 g of teicoplanin $A_2$ with 95.2% purity.

Therefore, it was noted that by using the method for purifying teicoplanin $A_2$ according to the present invention, it is possible to obtain a high purity teicoplanin $A_2$ pre-purification solution without using an excessive amount of organic solvents, even in a relatively simple process.

EXAMPLE 4

Preparation of High Purity Teicoplanin $A_2$ Purification Solution and Powder Thereof Using a Synthetic Adsorbent (Sold Under the Trademark DIAION HP2MG), Cation Exchange Resin (Sold Under the Trademark PUROLITE C145) and Reversed Phase Resin (Sold Under the Trademark SK-GEL ODS S15/30)

A high purity teicoplanin $A_2$ purification solution and powder thereof were prepared using the synthetic adsorbent (sold under the trademark DIAION HP2MG), the cation exchange resin (sold under the trademark PUROLITE C145) and reversed phase resin (sold under the trademark SK-GEL ODS S-15/30).

The primary pre-purification was performed using the synthetic adsorbent (sold under the trademark DIAION HP2MG), as described in Example 3. Next, for the secondary pre-purification, 190 ml of a sample solution containing about 1.15 g of teicoplanin $A_2$ was prepared.

100 ml of the cation exchange resin (sold under the trademark PUROLITE C145 (Purolite co.)) was packed in a chromatography column having a diameter of 4 cm and a length of 12 cm. The column was washed with sodium hydroxide and then acetic acid solution to equilibrate the resin. Purified water was eluted through the column and the eluent was checked to pH 5.55.

The sample solution was loaded on the column at a flow rate of 1.6 ml/min. The column was washed with purified water at room temperature and purified water which had been adjusted to pH 12 using sodium hydroxide (NaOH) solution was eluted through the column. The column used in the above procedure was regenerated with 150 ml of 1M NaOH solution and washed with 100 ml of purified water, 150 ml of 1M acetic acid and then, 200 ml of purified water.

The secondary purification solution obtained from the above-described procedures was subjected to HPLC to measure its purity. As a result, it was found to contain 1.11 g of teicoplanin $A_2$ with 48.7% purity.

Subsequently, for the final purification, 11 ml of a sample solution containing about 1.11 g of teicoplanin $A_2$ was prepared.

200 g of the reversed phase resin (sold under the trademark SK-GEL ODS S-15/30 (Soken co.)) was packed in a preparative HPLC column of NovaPrep 200 (Merck co.). The sample solution was loaded on the column at a flow rate of 50 ml/min. The column was washed with purified water at room temperature and purified water containing 23% acetonitrile was eluted through the column. The column used in the above procedure was regenerated with 300 ml of 90% methanol and washed with 500 ml of purified water.

The final purification solution obtained from the above-described procedures was subjected to HPLC to measure its purity. As a result, it was found to contain 0.9 g of teicoplanin $A_2$ with 95.5% purity.

In order to prepare powder from the high purity purification solution of teicoplanin $A_2$, a sample solution containing about 0.9 g of teicoplanin $A_2$ was prepared.

100 ml of the synthetic adsorbent (sold under the trademark DIAION HP2MG (Mitsubishi Chemical co.)) was packed in a chromatography column having a diameter of 4 cm and a length of 12 cm. The sample solution was loaded on the column at room temperature at a flow rate of 1.6 ml/min. Then, the column was washed with purified water at room temperature and purified water containing 60% acetonitrile was eluted through the column. The column used in the above procedure was washed with 300 ml of purified water.

The resulting eluent was concentrated in vacuum to remove acetonitrile and lyophilized to obtain teicoplanin $A_2$ powder.

EXAMPLE 5

Preparation of High Purity Teicoplanin $A_2$ Purification Solution and Powder Thereof Using a Synthetic Adsorbent (Sold Under the Trademark DIAION HP2MG), a Chelate Resin (Sold Under the Trademark DIAION CR11) and a Reversed Phase Resin (Sold Under the Trademark SHISEIDO DMS DM 1020)

A high purity teicoplanin $A_2$ purification solution and powder thereof were prepared using the synthetic adsorbent (sold under the trademark DIAION HP2MG), the chelate resin (sold under the trademark DIAION CR11) and the reversed phase resin (sold under the trademark SHISEIDO DMS DM 1020).

The primary pre-purification was performed using the synthetic adsorbent (sold under the trademark DIAION HP2MG), as described in Example 3 and the secondary pre-purification was also performed using the chelate resin (sold under the trademark DIAION CR11), as described in Example 3 subsequently, for the final purification, a sample Solution containing about 11 g of teicoplanin $A_2$ was prepared.

610 ml of the reversed phase resin (sold under the trademark SHISEIDO DMS DM 1020 (100-200 mesh, Shiseido Fine Chemical co.)) was packed in a chromatography column having a diameter of 4.8 cm and a length of 80 cm. The sample solution was loaded on the column at room temperature at a flow rate of 5.1 ml/min. Then, the column was washed with purified water at room temperature and purified water containing 25% acetonitrile was eluted through the column. The column used in the above procedure was regenerated with 1200 ml of 90% methanol and washed with 1800 ml of purified water.

The final eluent obtained from the above procedures was subjected to HPLC to measure its purity. As a result, it was found to contain 9 g of teicoplanin $A_2$ with 96.5% purity.

In order to prepare powder of teicoplanin $A_2$ from the high purity purification solution of teicoplanin $A_2$, a sample solution containing about 7 g of teicoplanin $A_2$ was prepared.

100 ml of the reversed phase resin (sold under the trademark SHISEIDO DMS DM 1020 (100-200 mesh, Shiseido Fine Chemical co.)) was packed in a chromatography column having a diameter of 4 cm and a length of 12 cm. The sample solution was loaded on the column at room temperature at a flow rate of 0.8 ml/min. Then, the column was washed with purified water at room temperature and purified water containing 70% acetone was eluted through the column. The column used in the above procedure was washed with 300 ml of purified water.

The resulting eluent was concentrated in vacuum to remove acetone and lyophilized to obtain teicoplanin $A_2$ powder.

Therefore, as shown in Example 4 and Example 5, it was noted that according to the method for purifying teicoplanin $A_2$ of the present invention, it is possible to obtain teicoplanin as powder by completely removing organic solvents through a simple freeze drying process, whereby the problems related to residual solvents in the precipitation after use of an organic solvent can be addressed.

As described above, according to the method for purifying teicoplanin $A_2$ of the present invention, it is possible to obtain teicoplanin $A_2$ with a much higher purity through a relatively simple process without using an excessive amount of an organic solvent.

Therefore, the method for purifying teicoplanin $A_2$ according to the present invention can be usefully used to industrially mass produce teicoplanin $A_2$.

What is claimed is:

1. A method for purifying teicoplanin $A_2$ comprising:
   (i) purifying a filtrate of a fermentation broth comprising teicoplanin $A_2$ on a synthetic polymeric adsorbent, to obtain a primary purification solution;
   (ii) purifying the primary purification solution on a cation exchange resin having a cross-linkage of over 8% resin; a chelate resin; or a resin selected from the group consisting of acidic porous resins comprising a styrene polymer matrix, acidic cation exchange resins comprising a porous styrene polymer matrix, and gel-type acidic polymer resins, to create a secondary purification solution;
   (iii) purifying the secondary purification solution on a reversed phase resin, to create a tertiary teicoplanin $A_2$ purification solution; and (iv) drying the tertiary teicoplanin $A_2$ purification solution to form a powder.

2. The method according to claim 1, wherein the synthetic polymeric adsorbent is chosen from porous styrene synthetic adsorbents, porous styrene synthetic adsorbents having bromine chemically substituted, porous styrene/divinyl polymers, macroreticularly cross-linked polymer, macroreticularly cross-linked aliphatic polymer, macroreticularly cross-linked aromatic polymer, methacrylic synthetic adsorbents, and carbonaceous synthetic adsorbents comprising a styrene/divinyl benzene ion exchange resin.

3. The method according to claim 1, wherein the synthetic polymeric adsorbent used in step (i) is eluted with purified water containing acetone in a concentration of 50 to 80%.

4. The method according to claim 1, wherein the resin used in the secondary purification step (ii) is regenerated by sequentially washing the resin with sodium hydroxide and a weak acid solution then, purified water so that the final eluate of purified water has a pH in the range of 4.5 to 7.0.

5. The method according to claim 1, wherein the resin used in the secondary purification step (ii) is eluted with purified water having a pH in the range of 10 to 13.

6. The method according to claim 1, wherein the reversed phase resin comprises a silica containing non-polar side chain having 1 to 18 carbons and having a particle size of 15 to 150 µm.

7. The method according to claim 1, wherein the reversed phase resin used in the tertiary purification step (iii) is purified water containing acetone or acetonitrile in a concentration of 20 to 30%.

8. The method according to claim 4, wherein the weak acid solution comprises acetic acid or diluted hydrochloric acid.

* * * * *